United States Patent
Chang (10) Patent No.: US 11,382,999 B2
(45) Date of Patent: Jul. 12, 2022

(54) ROTATIONAL AROMA DIFFUSER STRUCTURE

(71) Applicant: Chin-Tan Chang, Taichung (TW)

(72) Inventor: Chin-Tan Chang, Taichung (TW)

(*) Notice: Subject to any disclaimer, the term of this patent is extended or adjusted under 35 U.S.C. 154(b) by 217 days.

(21) Appl. No.: 16/928,240

(22) Filed: Jul. 14, 2020

(65) Prior Publication Data
US 2021/0128771 A1 May 6, 2021

(30) Foreign Application Priority Data
Nov. 1, 2019 (TW) .................. 108214486

(51) Int. Cl.
*A61L 9/12* (2006.01)
(52) U.S. Cl.
CPC .............. *A61L 9/12* (2013.01); *A61L 2209/15* (2013.01)
(58) Field of Classification Search
CPC ............................... A61L 9/12; A61L 2209/15

USPC ...................................... 239/53–60
See application file for complete search history.

(56) References Cited

U.S. PATENT DOCUMENTS

2006/0049270 A1* 3/2006 Wayne ..................... A47F 5/02
239/57

* cited by examiner

*Primary Examiner* — Christopher S Kim
(74) *Attorney, Agent, or Firm* — Alan D. Kamrath; Karin L. Williams; Mayer & Williams PC (57) ABSTRACT

An aroma diffuser structure includes a base, a holding member, a frame, an adjusting member, and an aroma diffuser. The holding member is mounted on the base and has a screw hole. The frame is mounted on the holding member and has an upper portion provided with a first magnetic member. The adjusting member has an external threaded section extending through the frame and screwed through the screw hole of the holding member. The aroma diffuser has a plurality of air vents. The aroma diffuser is rotatable on the adjusting member and has a top provided with a rotation shaft which is provided with a second magnetic member magnetically attracted with the first magnetic member.

7 Claims, 7 Drawing Sheets

ROTATIONAL AROMA DIFFUSER STRUCTURE

BACKGROUND OF THE INVENTION

1. Field of the Invention

The present invention relates to a diffuser and, more particularly, to an aroma diffuser structure to spread and diffuse aroma or fragrance.

2. Description of the Related Art

A conventional aroma diffuser comprises a bottle, an essential oil contained in the bottle, and a cover removably mounted on the bottle to cover the essential oil. After the cover is removed from the bottle, the perfume of the essential oil is diffused outward to provide a comfortable sensation to the user. However, the bottle is disposed at a stationary state, so that the diffusion effect of the essential oil is poor and limited. In addition, the conventional aroma diffuser only has a single function and cannot provide an amusement effect.

BRIEF SUMMARY OF THE INVENTION

The primary objective of the present invention is to provide a rotational aroma diffuser structure with a swivelable (or rotatable) aroma diffuser.

In accordance with the present invention, there is provided an aroma diffuser structure comprising a base, a holding member, a frame, an adjusting member, and an aroma diffuser. The base has a top face and a bottom face. The top face and the bottom face of the base are disposed at a horizontal state. The top face of the base has a central position provided with an axial hole. The axial hole of the base disposed at a vertical state. The holding member has a lower end provided with a fixed portion and an upper end provided with a connecting portion. The fixed portion of the holding member is secured in the axial hole of the base. The fixed portion of the holding member has an outer diameter flush with an inner diameter of the axial hole of the base. The holding member has an interior provided with a screw hole. The frame has a lower portion provided with a connecting hole. The connecting hole of the frame is mounted on the connecting portion of the holding member. The frame has an upper portion provided with a cavity. A first magnetic member is mounted in the cavity of the frame. The adjusting member has a lower portion provided with an external threaded section. The external threaded section of the adjusting member extends through the connecting hole of the frame and is screwed through the screw hole of the holding member. The adjusting member has an upper portion provided with a flat face. The aroma diffuser has an interior receiving an aromatic member. The aroma diffuser is provided with a plurality of air vents, and fragrant odors of the aromatic member are diffused outward from the air vents of the aroma diffuser. The aroma diffuser has a bottom provided with a conic portion placed on the flat face of the adjusting member. The aroma diffuser has a top provided with a rotation shaft. The rotation shaft of the aroma diffuser has an interior provided with a receiving recess. A second magnetic member is mounted in the receiving recess of the rotation shaft and corresponds to the first magnetic member. The opposite sides of the first magnetic member and the second magnetic member have different polarities, such that the first magnetic member and the second magnetic member are magnetically attracted with each other.

According to the primary advantage of the present invention, the aroma diffuser is rotated during a long period of time so as to diffuse the fragrant odor completely.

According to another advantage of the present invention, the aroma diffuser is rotated successively to provide an amusement effect to the user during diffusion of the scent.

Further benefits and advantages of the present invention will become apparent after a careful reading of the detailed description with appropriate reference to the accompanying drawings.

DETAILED DESCRIPTION OF THE INVENTION

Figure 1:
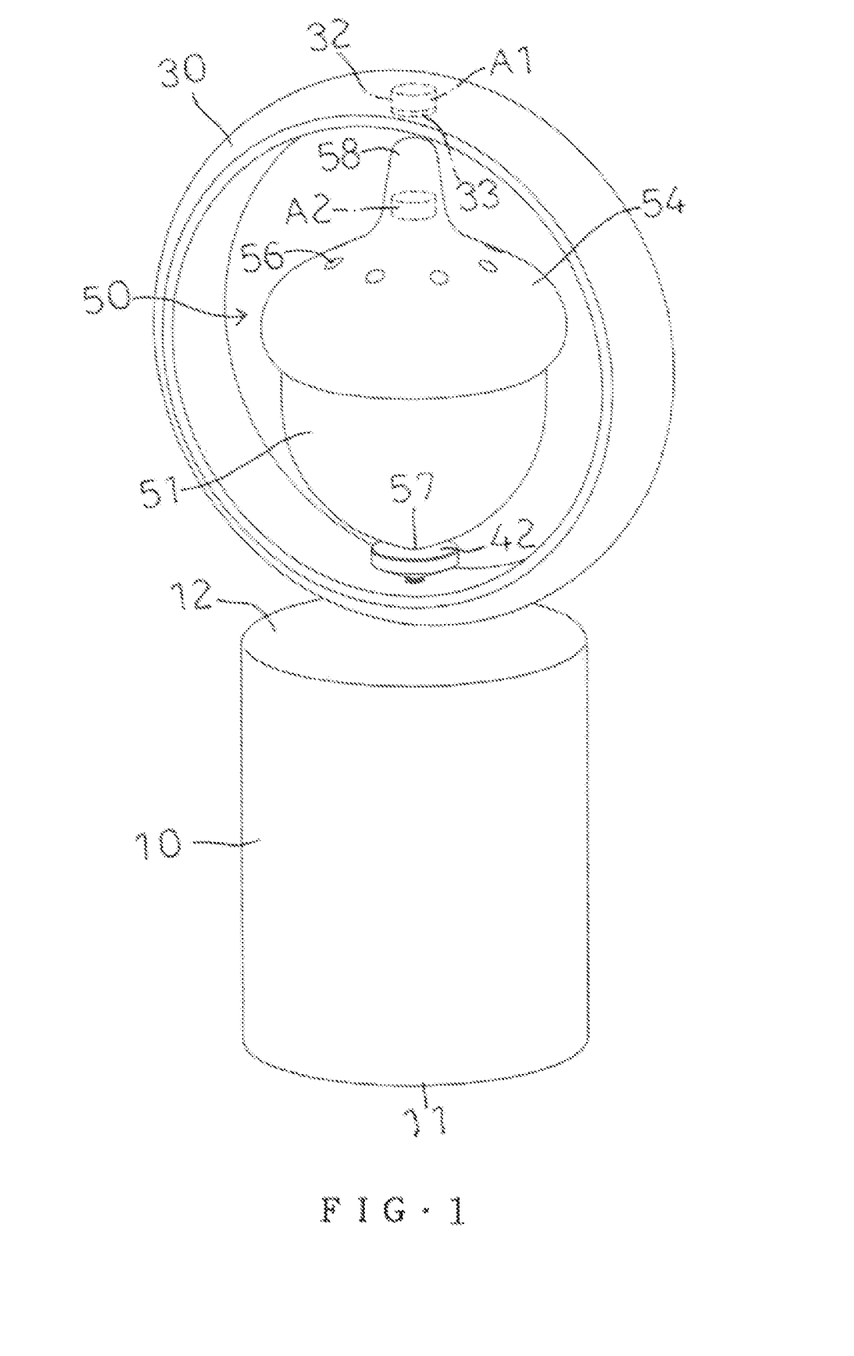
FIG. 1 is a perspective view of an aroma diffuser structure in accordance with the preferred embodiment of the present invention.
Figure 2:
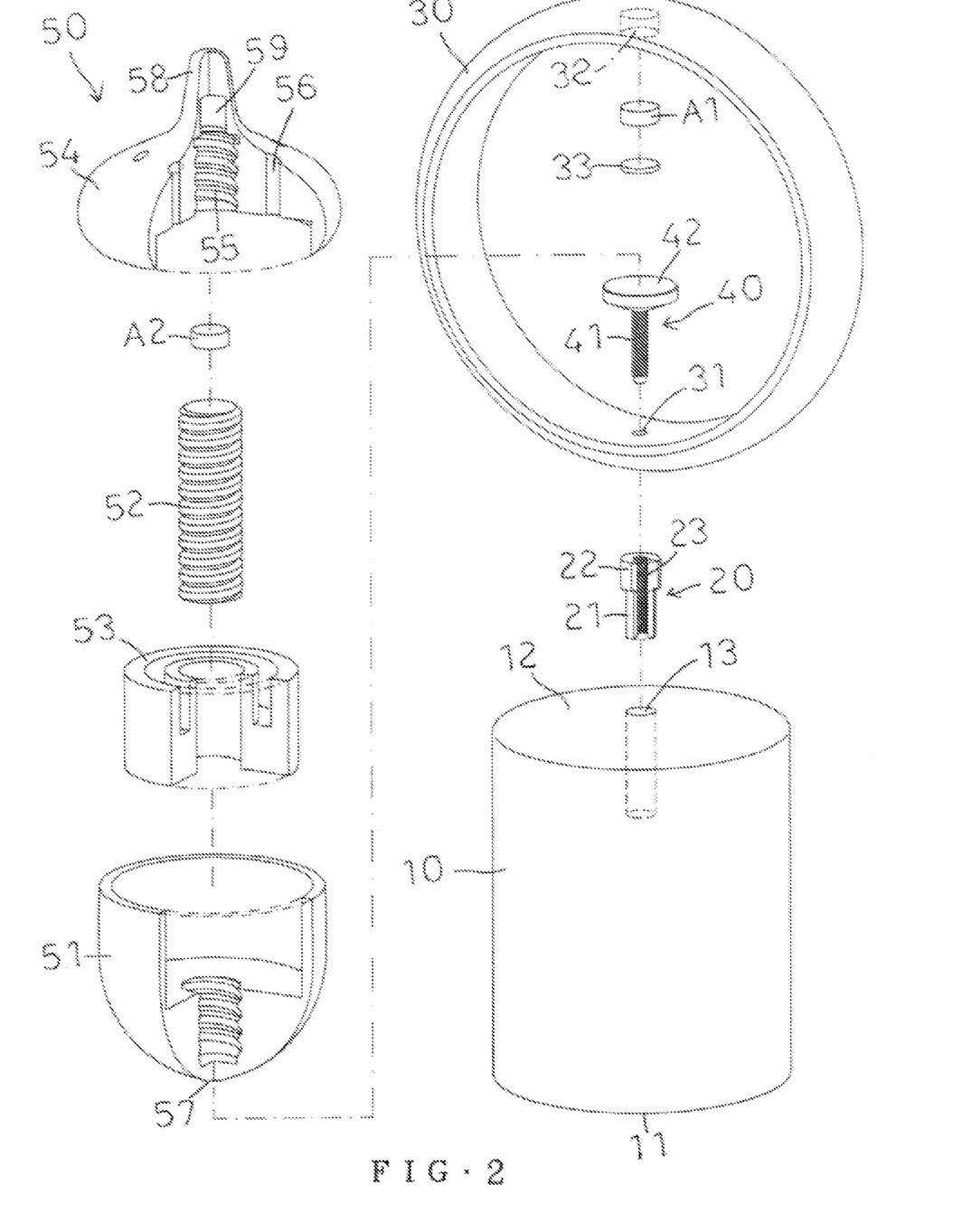
FIG. 2 is an exploded perspective view of the aroma diffuser structure in accordance with the preferred embodiment of the present invention.
Figure 3:
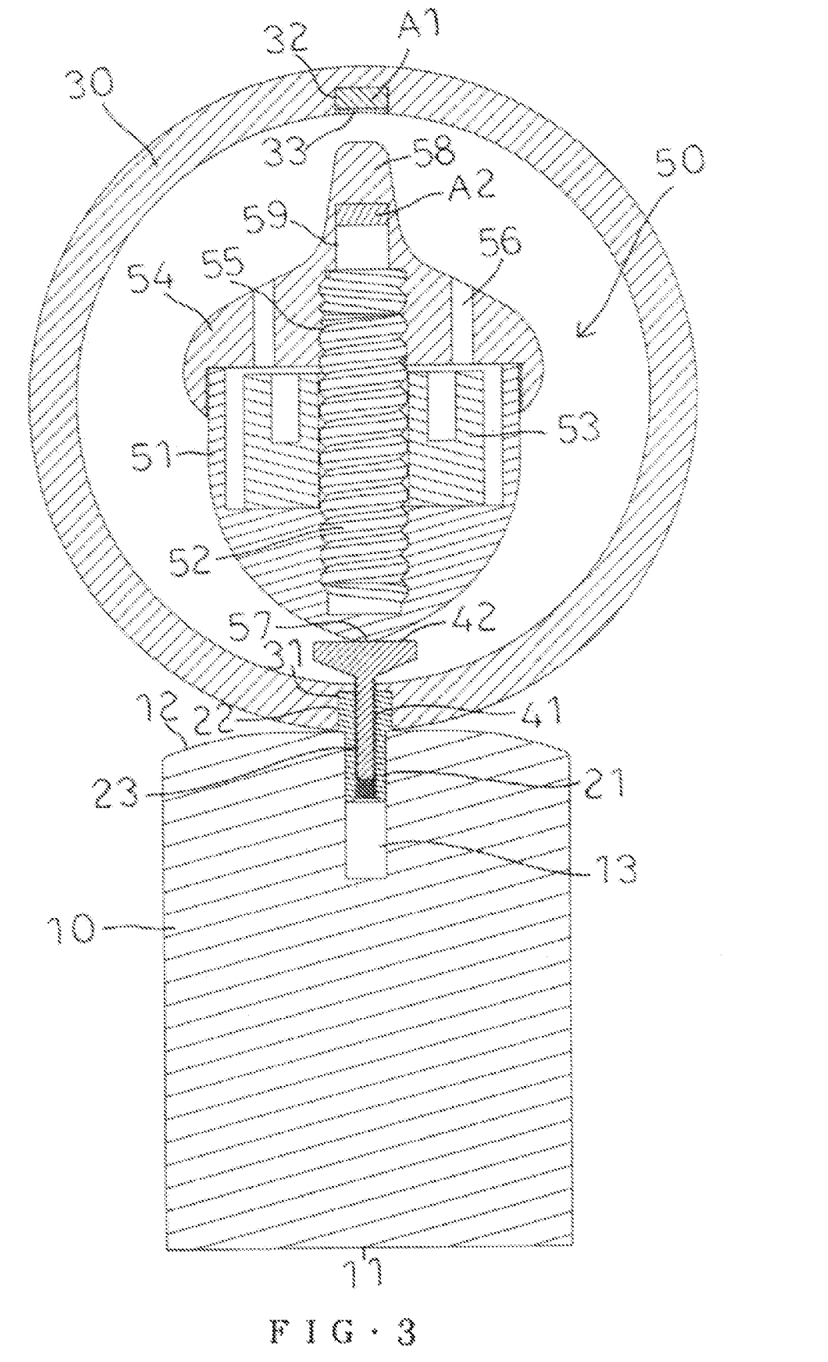
FIG. 3 is a front cross-sectional view of the aroma diffuser structure as shown in FIG. 1.

Referring to the drawings and initially to FIGS. 1-3, an aroma diffuser structure in accordance with the preferred embodiment of the present invention comprises a base 10, a holding member 20, a frame 30, an adjusting member 40, and an aroma diffuser 50.

The base 10 has a top face 12 and a bottom face 11. The top face 12 and the bottom face 11 of the base 10 are disposed at a horizontal state. The top face 12 of the base 10 has a central position provided with an axial hole 13. The axial hole 13 of the base 10 disposed at a vertical state.

The holding member 20 is mounted on the base 10 and has a lower end provided with a fixed portion 21 and an upper end provided with a connecting portion 22. The fixed portion 21 of the holding member 20 is secured in the axial hole 13 of the base 10. The fixed portion 21 of the holding member 20 has an outer diameter flush with an inner diameter of the axial hole 13 of the base 10. The holding member 20 has an interior provided with a screw hole 23. The screw hole 23 extends through a whole length of the holding member 20. The connecting portion 22 of the holding member 20 is larger than the axial hole 13 of the base 10 and rests on the top face 12 of the base 10. The connecting portion 22 of the holding member 20 has an outer diameter more than that of the fixed portion 21.

The frame 30 is mounted on the holding member 20 and has a lower portion connected with the connecting portion 22 of the holding member 20. The lower portion of the frame 30 is provided with a connecting hole 31. The connecting hole 31 of the frame 30 is mounted on the connecting portion 22 of the holding member 20 and corresponds to the screw hole 23 of the holding member 20. The frame 30 has an upper portion provided with a cavity 32. The connecting hole 31 and the cavity 32 construct a central axis of the frame 30.

A first magnetic member A1 is mounted in the cavity 32 of the frame 30.

The adjusting member 40 has a lower portion provided with an external threaded section 41. The external threaded section 41 of the adjusting member 40 extends through the connecting hole 31 of the frame 30 and is screwed through the screw hole 23 of the holding member 20. The adjusting member 40 has an upper portion provided with a flat face 42.

The aroma diffuser 50 has an interior receiving an aromatic member. The aroma diffuser 50 is provided with a plurality of air vents 56, and fragrant odors of the aromatic member are diffused outward from the air vents 56 of the aroma diffuser 50. The aroma diffuser 50 has a bottom provided with a conic (or tapered or pointed) portion 57 placed on the flat face 42 of the adjusting member 40. The aroma diffuser 50 has a top provided with a rotation shaft 58. The rotation shaft 58 of the aroma diffuser 50 has an interior provided with a receiving recess 59. The rotation shaft 58 of the aroma diffuser 50 is in line with the conic portion 57, such that the rotation shaft 58 and the conic portion 57 construct an axis of the aroma diffuser 50. Thus, the aroma diffuser 50 is revolved about the rotation shaft 58 and the conic portion 57 of the aroma diffuser 50.

A second magnetic member A2 is mounted in the receiving recess 59 of the rotation shaft 58 and corresponds to the first magnetic member A1. The opposite sides of the first magnetic member A1 and the second magnetic member A2 have different polarities, such that the first magnetic member A1 and the second magnetic member A2 are magnetically attracted with each other.

In the preferred embodiment of the present invention, the base 10 is made of wood (or plastic) material, the frame 30 is made of wood (or plastic) material, and the aroma diffuser 50 is made of wood (or plastic) material.

In the preferred embodiment of the present invention, the base 10 has a geometric shape, including a cylinder, a cube, a cuboid or the like.

In the preferred embodiment of the present invention, the frame 30 has a geometric shape, including a circular hollow, a rectangular hollow, a C-shaped hollow, a heart-shaped hollow or the like.

In the preferred embodiment of the present invention, a closure (or seal) 33 is mounted in the cavity 32 of the frame 30 to seal and secure the first magnetic member A1.

In the preferred embodiment of the present invention, the aromatic member of the aroma diffuser 50 contains a solid aroma diffusion substance 1 (see FIG. 6), including an insect repellent, an aromatic agent, a brain energizer (or stimulant) or the like.

In the preferred embodiment of the present invention, the aromatic member of the aroma diffuser 50 contains a liquid aroma diffusion substance 2 (see FIG. 7), including essential oil or the like.

In the preferred embodiment of the present invention, the aroma diffuser 50 includes a main body 51, a threaded rod 52, a receiving disk 53, and a cover 54. The main body 51 is used to receive the solid aroma diffusion substance 1. The conic portion 57 of the aroma diffuser 50 is formed on the bottom of the main body 51. The receiving disk 53 is removably mounted in the main body 51. The receiving disk 53 is used to receive the liquid aroma diffusion substance 2. The threaded rod 52 is secured in a central portion of the main body 51 and extends through the receiving disk 53. The cover 54 has a central portion provided with a screw bore 55 screwed onto the threaded rod 52 to cover the receiving disk 53. The air vents 56 of the aroma diffuser 50 are formed on the periphery of the cover 54. The rotation shaft 58 of the aroma diffuser 50 is formed on a central position of the top of the cover 54.

Figure 4:
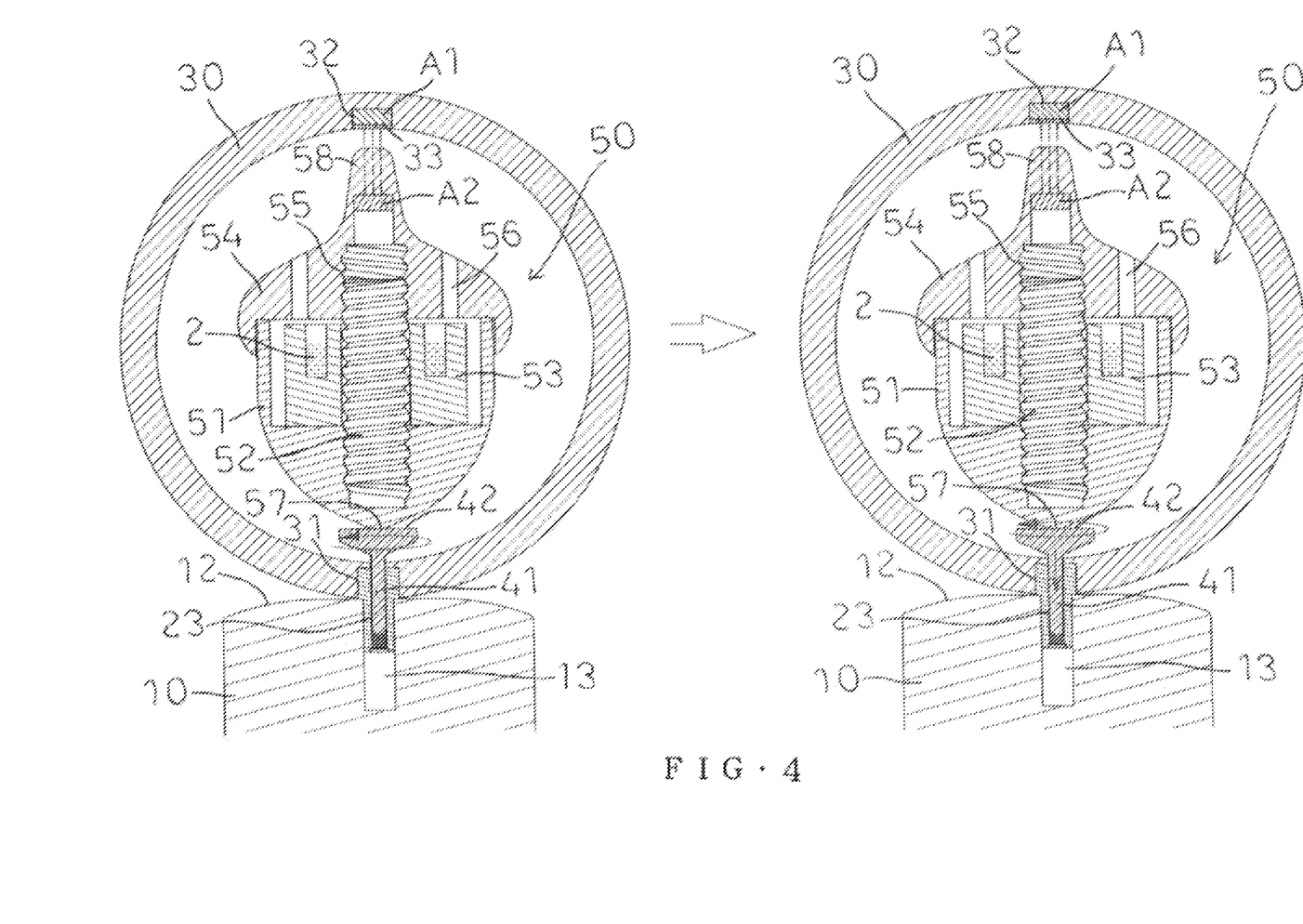
FIG. 4 are schematic operational views of the aroma diffuser structure as shown in FIG. 3 in adjustment.

In adjustment, referring to FIG. 4 with reference to FIGS. 1-3, when the adjusting member 40 is rotated, the external threaded section 41 of the adjusting member 40 is moved in the screw hole 23 of the holding member 20, such that the flat face 42 of the adjusting member 40 is moved to lift or lower the aroma diffuser 50, so as to adjust the distance between the second magnetic member A2 and the first magnetic member A1. In such a manner, when the aroma diffuser 50 is lifted as shown in the left side of FIG. 4, the second magnetic member A2 is moved toward the first magnetic member A1 to decrease the distance between the second magnetic member A2 and the first magnetic member A1, such that the magnetically attractive force between the second magnetic member A2 and the first magnetic member A1 is increased. On the contrary, when the aroma diffuser 50 is lowered as shown in the right side of FIG. 4, the second magnetic member A2 is moved away from the first magnetic member A1 to increase the distance between the second magnetic member A2 and the first magnetic member A1, such that magnetically attractive force between the second magnetic member A2 and the first magnetic member A1 is decreased. Thus, the distance between the second magnetic member A2 and the first magnetic member A1 is adjusted to reach the optimum value under which the gravity of the aroma diffuser 50 is balanced by the magnetically attracting force between the second magnetic member A2 and the first magnetic member A1, such that the aroma diffuser 50 produces a magnetically levitating effect, so as to reduce the friction between the conic portion 57 of the aroma diffuser 50 and the flat face 42 of the adjusting member 40 to the minimum during rotation of the aroma diffuser 50.

Figure 5:
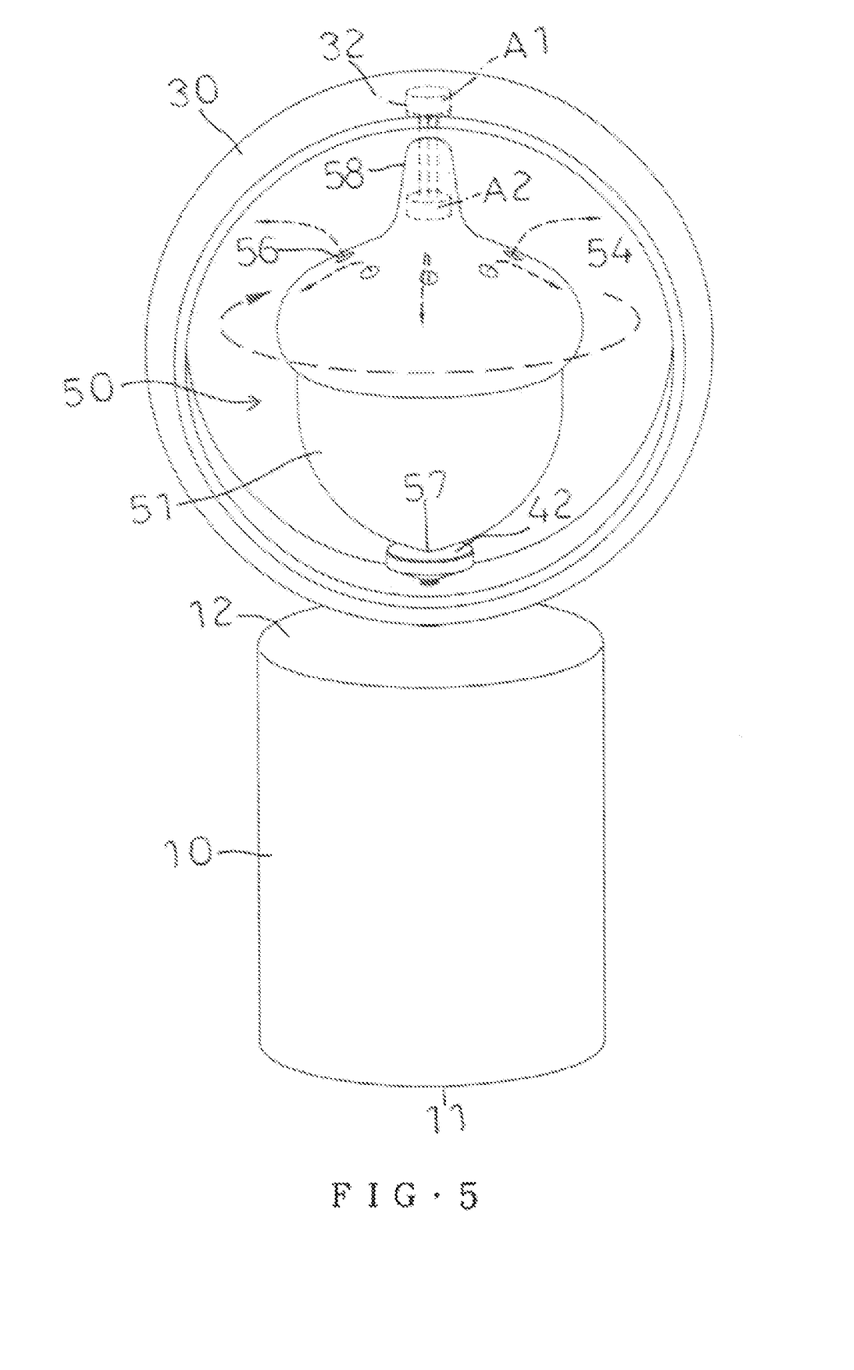
FIG. 5 is a schematic operational view of the aroma diffuser structure as shown in FIG. 1 in use.

In operation, referring to FIG. 5 with reference to FIGS. 1-4, when the aroma diffuser 50 is rotated on the flat face 42 of the adjusting member 40, the scent of the aromatic member of the aroma diffuser 50 is diffused outward from the air vents 56 of the aroma diffuser 50. At this time, the aroma diffuser 50 is levitated by the magnetically attracting force between the second magnetic member A2 and the first magnetic member A1, such that when the aroma diffuser 50 is rotated along the central axis thereof, the friction between the conic portion 57 of the aroma diffuser 50 and the flat face 42 of the adjusting member 40 has the minimum value. Thus, the aroma diffuser 50 is rotated successively during a long period of time, at least more than many ten minutes, such that the fragrance of the aromatic member of the aroma diffuser 50 is diffused completely.

Figure 6:
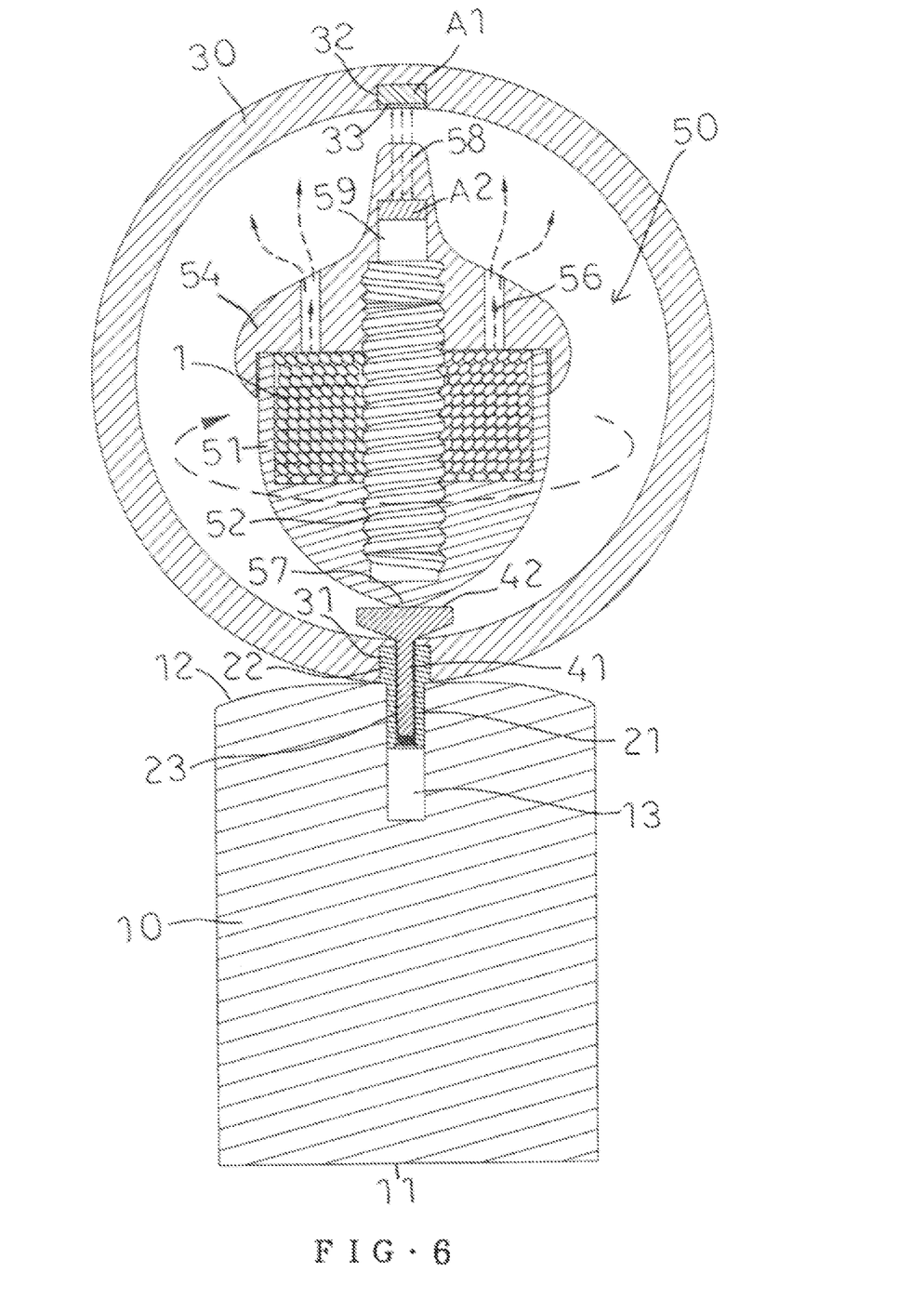
FIG. 6 is a cross-sectional view showing the aroma diffuser structure using a solid aroma diffusion substance.

In practice, referring to FIG. 6 with reference to FIGS. 1-5, after the receiving disk 53 is removed from the main body 51, the solid aroma diffusion substance 1 is directly received in the main body 51. Thus, the solid aroma diffusion substance 1 emits a special odor to repel insects.

Figure 7:
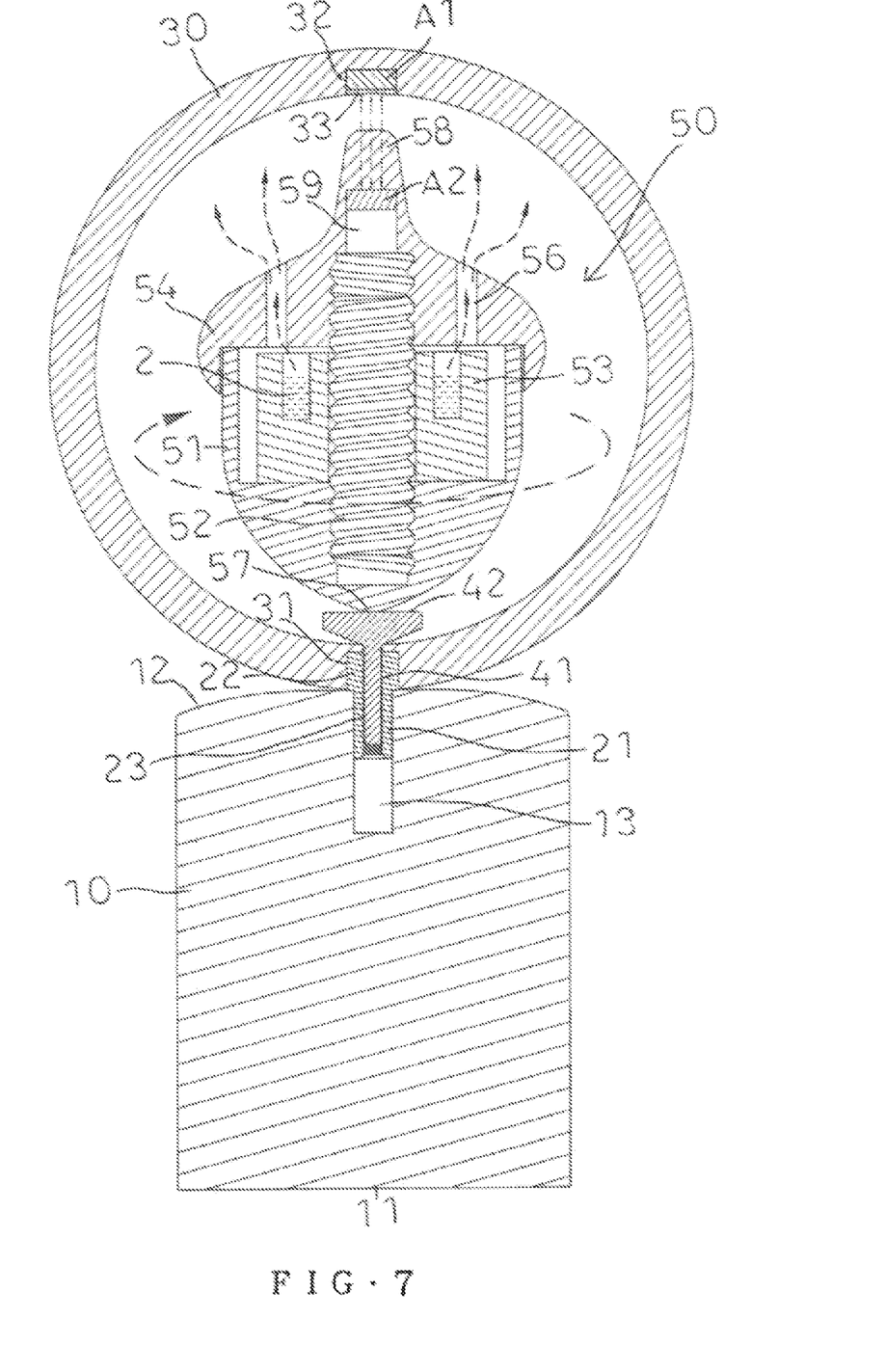
FIG. 7 is a cross-sectional view showing the aroma diffuser structure using a liquid aroma diffusion substance.

Alternatively, referring to FIG. 7 with reference to FIGS. 1-5, when the receiving disk 53 is mounted in the main body 51, the liquid aroma diffusion substance 2 is stored in the receiving disk 53. Thus, the liquid aroma diffusion substance 2 emits an aroma or a fresh air to release the user's pressure.

Accordingly, the aroma diffuser 50 is rotated during a long period of time so as to diffuse the fragrant odor completely. In addition, the aroma diffuser 50 is rotated successively to provide an amusement effect to the user during diffusion of the scent.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the scope of the invention.

The invention claimed is:

1. An aroma diffuser structure comprising:
a base, a holding member, a frame, an adjusting member, and an aroma diffuser;
wherein:
the base has a top face and a bottom face;
the top face and the bottom face of the base are disposed at a horizontal state;
the top face of the base has a central position provided with an axial hole;
the axial hole of the base disposed at a vertical state;
the holding member has a lower end provided with a fixed portion and an upper end provided with a connecting portion;
the fixed portion of the holding member is secured in the axial hole of the base;
the fixed portion of the holding member has an outer diameter flush with an inner diameter of the axial hole of the base;
the holding member has an interior provided with a screw hole;
the frame has a lower portion provided with a connecting hole;
the connecting hole of the frame is mounted on the connecting portion of the holding member;
the frame has an upper portion provided with a cavity;
a first magnetic member is mounted in the cavity of the frame;
the adjusting member has a lower portion provided with an external threaded section;
the external threaded section of the adjusting member extends through the connecting hole of the frame and is screwed through the screw hole of the holding member;
the adjusting member has an upper portion provided with a flat face;
the aroma diffuser has an interior receiving an aromatic member;
the aroma diffuser is provided with a plurality of air vents, and fragrant odors of the aromatic member are diffused outward from the air vents of the aroma diffuser;
the aroma diffuser has a bottom provided with a conic portion placed on the flat face of the adjusting member;
the aroma diffuser has a top provided with a rotation shaft;
the rotation shaft of the aroma diffuser has an interior provided with a receiving recess;
a second magnetic member is mounted in the receiving recess of the rotation shaft and corresponds to the first magnetic member; and
opposite sides of the first magnetic member and the second magnetic member have different polarities, such that the first magnetic member and the second magnetic member are magnetically attracted with each other.

2. The aroma diffuser structure as claimed in claim 1, wherein the base is made of wood material, the frame is made of wood material, and the aroma diffuser is made of wood material.

3. The aroma diffuser structure as claimed in claim 1, wherein the base has a geometric shape, including a cylinder, a cube or a cuboid.

4. The aroma diffuser structure as claimed in claim 1, wherein the frame has a geometric shape, including a circular hollow, a rectangular hollow, a C-shaped hollow or a heart-shaped hollow.

5. The aroma diffuser structure as claimed in claim 1, wherein a closure is mounted in the cavity of the frame to seal and secure the first magnetic member.

6. The aroma diffuser structure as claimed in claim 1, wherein the aromatic member of the aroma diffuser contains a solid aroma diffusion substance.

7. The aroma diffuser structure as claimed in claim 1, wherein the aromatic member of the aroma diffuser contains a liquid aroma diffusion substance.

* * * * *